US006953587B2

(12) United States Patent
Dufton et al.

(10) Patent No.: US 6,953,587 B2
(45) Date of Patent: Oct. 11, 2005

(54) PROCESS FOR MAKING A WATER-SOLUBLE FOAM COMPONENT

(75) Inventors: Daniel James Dufton, Newcastle Upon Tyne (GB); Simon Howe, South Shields (GB)

(73) Assignee: Proacter & Gamble Company, Cincinnati, OH (US)

( * ) Notice: Subject to any disclaimer, the term of this patent is extended or adjusted under 35 U.S.C. 154(b) by 100 days.

(21) Appl. No.: 10/447,393

(22) Filed: May 29, 2003

(65) Prior Publication Data

US 2003/0216485 A1 Nov. 20, 2003

Related U.S. Application Data

(63) Continuation of application No. 09/951,910, filed on Sep. 13, 2001, now abandoned.

(30) Foreign Application Priority Data

Sep. 13, 2000 (GB) .............................................. 0022525

(51) Int. Cl.$^7$ .................................................. C08J 9/30
(52) U.S. Cl. .................... 424/434; 424/435; 514/772.3; 514/772.6; 514/944; 521/65; 521/141
(58) Field of Search ................................. 424/434, 435; 514/772.3, 772.6, 944; 521/65, 141

(56) References Cited

U.S. PATENT DOCUMENTS

| 3,128,287 A | 4/1964 | Berg |
| 3,159,581 A | 12/1964 | Diehl |
| 3,213,030 A | 10/1965 | Diehl |
| 3,234,258 A | 2/1966 | Morris |
| 3,308,067 A | 3/1967 | Diehl |
| 3,400,148 A | 9/1968 | Quimby |
| 3,422,021 A | 1/1969 | Roy |
| 3,422,137 A | 1/1969 | Quimby |
| 3,519,570 A | 7/1970 | McCarty |
| 3,533,139 A | 10/1970 | Gomes et al. |
| 3,635,830 A | 1/1972 | Lamberti et al. |
| 3,723,322 A | 3/1973 | Diehl |
| 3,893,929 A | 7/1975 | Basadur |
| 3,923,679 A | 12/1975 | Rapko |
| 3,929,678 A | 12/1975 | Laughlin et al. |
| 3,959,230 A | 5/1976 | Hays |
| 4,000,093 A | 12/1976 | Nicol et al. |
| 4,088,610 A | 5/1978 | Bevan et al. |
| 4,102,903 A | 7/1978 | Crutchfield et al. |
| 4,120,874 A | 10/1978 | Crutchfield et al. |
| 4,144,226 A | 3/1979 | Crutchfield et al. |
| 4,158,635 A | 6/1979 | Crutchfield et al. |
| 4,174,291 A | 11/1979 | Benjamin et al. |
| 4,201,824 A | 5/1980 | Violland et al. |
| 4,220,918 A | 9/1980 | Pepper |
| 4,240,918 A | 12/1980 | Lagasse et al. |
| 4,525,524 A | 6/1985 | Tung et al. |
| 4,548,744 A | 10/1985 | Connor |
| 4,565,647 A | 1/1986 | Llenado |
| 4,566,984 A | 1/1986 | Bush |
| 4,579,681 A | 4/1986 | Ruppert et al. |
| 4,597,898 A | 7/1986 | Vander Meer |
| 4,663,071 A | 5/1987 | Bush et al. |
| 4,663,358 A | 5/1987 | Hyon et al. |
| 4,702,857 A | 10/1987 | Gosselink |
| 4,711,730 A | 12/1987 | Gosselink et al. |
| 4,721,580 A | 1/1988 | Gosselink |
| 4,734,097 A | 3/1988 | Tanabe et al. |
| 4,746,456 A | 5/1988 | Kud et al. |
| 4,771,730 A | 9/1988 | Tezuka |
| 4,787,989 A | 11/1988 | Fanelli et al. |
| 4,810,414 A | 3/1989 | Huge-Jensen et al. |
| 4,861,512 A | 8/1989 | Gosselink |
| 4,877,896 A | 10/1989 | Maldonado et al. |
| 4,925,577 A | 5/1990 | Borcher, Sr. et al. |
| 4,925,588 A | 5/1990 | Berrod et al. |
| 4,956,447 A | 9/1990 | Gosselink et al. |
| 4,968,451 A | 11/1990 | Scheibel et al. |
| 4,976,879 A | 12/1990 | Maldonado et al. |
| 5,075,041 A | 12/1991 | Lutz |
| 5,182,043 A | 1/1993 | Morrall et al. |
| 5,207,941 A | 5/1993 | Kroner et al. |
| 5,349,101 A | 9/1994 | Lutz et al. |
| 5,389,277 A | 2/1995 | Prieto |
| 5,415,807 A | 5/1995 | Gosselink et al. |
| 5,434,192 A | 7/1995 | Thach et al. |
| 5,454,982 A | 10/1995 | Murch et al. |
| 5,458,884 A | 10/1995 | Britton et al. |
| 5,489,393 A | 2/1996 | Connor et al. |
| 5,565,145 A | 10/1996 | Watson et al. |
| 5,599,782 A | 2/1997 | Pan et al. |
| 5,691,298 A | 11/1997 | Gosselink et al. |
| 5,728,671 A | 3/1998 | Rohrbaugh et al. |
| 5,834,412 A | 11/1998 | Rohrbaugh et al. |
| 5,843,878 A | 12/1998 | Gosselink et al. |

FOREIGN PATENT DOCUMENTS

| DE | 2 126 161 | 12/1971 |
| DE | 1 269 839 | 4/1972 |
| EP | 0 111 965 B1 | 6/1984 |
| EP | 0 111 984 B1 | 6/1984 |
| EP | 0 112 592 B1 | 7/1984 |
| EP | 0 218 272 B1 | 4/1987 |
| EP | 0 258 068 B1 | 3/1988 |
| GB | 929877 | 6/1963 |
| WO | WO 95/26397 A1 | 10/1995 |
| WO | WO 96/23873 A1 | 8/1996 |
| WO | WO 97/32961 A2 | 9/1997 |

*Primary Examiner*—Morton Foelak
(74) *Attorney, Agent, or Firm*—James F. McBride; Kim W. Zerby; Steve W. Miller

(57) ABSTRACT

The present invention relates to a process for preparing a water-soluble foam matrix which is capable of delivering an active ingredient and articles of manufacture comprising said foam matrix, said article comprising:
  i) a water-soluble polymeric component in the form of a foam matrix; and
  ii) an active ingredient component dispersed throughout said matrix;
  said process comprising the steps of:
  a) admixing a water-soluble polymer and an active ingredient to form a homogeneous admixture, said admixture having a viscosity of at least 150 Pa-sec;
  b) introducing a gas or a compound capable of releasing a gas into said admixture to form a foam matrix; and
  c) optionally, shaping said matrix to provide a matrix having a shape or a form.

39 Claims, No Drawings

US 6,953,587 B2

PROCESS FOR MAKING A WATER-SOLUBLE FOAM COMPONENT

CROSS REFERENCE TO RELATED APPLICATIONS

This application is a continuation under 35 U.S.C. §120 of U.S. application Ser. No. 09/951,910 filed on Sep. 13, 2001 now abandoned, which in turn claims priority under 35 U.S.C. §119(a)–(d) or §365(b) to GB 0022525.0, filed Sep. 13, 2000.

FIELD OF THE INVENTION

The present invention relates to a process for preparing a water-soluble foam matrix which is capable of delivering an active ingredient. The present invention further relates to an article of manufacture which is a water-soluble foam prepared by the herein described process.

BACKGROUND OF THE INVENTION

Delivery of active ingredients to a situs is the primary goal of most product formulators. The active ingredient may have many forms, inter alia, surfactants, pharmaceuticals, skin care agents. The controlled release of active ingredients is key to the consumer gaining the maximal benefit of the active ingredient. Indeed, the form in which the active is delivered must be practical and utilitarian. For example, facial soap is delivered as a flowable liquid or as a solid bar, but not typically in the form of a free flowing granule as are laundry soaps.

There is no controllably water-soluble delivery system for delivery of active ingredients, which can provide the options of a unitized dose, as well as an article which the consumer can proportion either by cleavage, breaking, cutting or other means of fracturing of the article, or by length of time of use.

There is therefore a long felt need in the art for a new form of delivering an active ingredient which provides the formulator with options for delivering to a situs an active ingredient which delivery is controlled by the relative water solubility of the matrix from which said active is provided.

SUMMARY OF THE INVENTION

The present invention meets the aforementioned need in that it has been surprisingly discovered that active ingredients, inter alia, surfactants, pharmaceuticals, laundry adjuncts, personal care ingredients, can be delivered in a controllable water-soluble manner. The present invention relates to articles of manufacture which are water-soluble and which upon solublization in water are capable of releasing to a situs a composition having as the major component at least one active ingredient. The articles may take any shape or form. The articles may be used or consumed in one application (unitized dose) or used as needed by the consumer.

The first aspect of the present invention relates to a process for preparing the articles of manufacture, said articles comprising:

i) a water-soluble polymeric component in the form of a foam matrix; and ii) an active ingredient component dispersed throughout said matrix;

said process comprising the steps of:

a) admixing a water-soluble polymer and an active ingredient to form a homogeneous admixture, said admixture having a viscosity of at least 150 Pa-sec;

b) introducing a gas or a compound capable of releasing a gas into said admixture to form a foam matrix; and c) optionally, shaping said matrix to provide a matrix having a shape or a form.

The present invention further relates to articles of manufacture which comprise a water-soluble foam matrix and which are capable of effectively releasing to a situs an active ingredient in a controllable manner.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to articles of manufacture and a process for making said articles. The long felt need for delivery of a liquid active ingredient by way of a solid, water soluble matrix has been overcome by the process and articles of manufacture described herein.

Step (a) of the process relates to forming a homogeneous admixture of a water-soluble polymeric material and one or more active ingredients. The homogeneous admixture is formed into a foam matrix in a subsequent process step.

Step (a) requires the admixture formed to have a viscosity of at least 150 Pa-sec (Pascal seconds). In another embodiment of the present invention, the final admixture viscosity is at least 200 Pa-sec, whereas other embodiments require higher viscosities, for example, one embodiment relates to a viscosity of 300 Pa-sec while another relates to a viscosity of 350 Pa-sec.

When defining the above viscosity levels, the measurements are made at 25° C. and a shear rate of 1.7 sec$^{-1}$. However, when measured at 25° C. and a shear rate of 10 sec$^{-1}$, the lowest viscosity is at least 100 Pa-sec. When measuring viscosity at different temperatures and shear rates, the formulator will adjust the viscosity values such that the lowest viscosity is comparable to 150 Pa-sec at the hereinabove defined conditions.

The water-soluble polymer which is introduced into the process at step (a) can be any suitable polymer or monomer which copolymerizes with other monomers during optional steps of the present process, which is capable of forming a water soluble matrix. Non-limiting examples of water-soluble polymers include polymers selected from the group consisting of polyvinyl alcohol, polyvinyl pyrrolidone, polyalkylene oxides, cellulose ethers, polycarboxylic acids, polyamino acids, polyacrylamide, and mixtures thereof. One embodiment of the present invention relates to polymers which are polyvinyl alcohol, hydroxypropyl methylcellulose, maleic/acrylic acid copolymers, and mixtures thereof.

On aspect of the present invention relates to a process wherein polyvinyl alcohol is the water-soluble polymer. The formulator can purchase or prepare polyvinyl alcohol having a molecular weight and bulk modulus such that when combined with the one or more active ingredients, the viscosity requirements of the embodiments of the present invention are met or exceeded. Polyvinyl alcohol is available in all forms, from semi-free flowing liquid to powder. In the case wherein polyvinyl alcohol is a solid, a co-solvent or plasticizer can be added which can be removed in an optional processing step or carried into the final product.

One embodiment of the present invention utilizes water as a solvent, co-solvent, or plasticizer. The amount of added liquid can be determined by the needs of the formulator provided the 150 Pa-sec viscosity minimum of the homogeneous admixture is met. Non-limiting examples of solvents include water, $C_1$–$C_6$ alcohols, and the like.

The purpose of the present invention is to deliver an active ingredient to a situs. The term "situs" is defined herein as "any location which can be affected by the use of the foam matrices of the present invention and not restricted to direct contact thereby." For example, an article of manufacture produced by the present process can be used to deliver a skin conditioning agent directly to skin by contacting the article in the presence of water with human skin. Or the article may be a unitized dose which is added to a container of water to provide a measured amount of an active ingredient, a surfactant, inter alia. One variation of this last embodiment can have the article take the form of free flowing particles.

Without suggesting limitation, the active ingredients can derive from any active category, for example:

i) said active ingredient is a detersive surfactant selected from the group consisting of anionic, cationic, nonionic, zwitterionic, ampholytic surfactants and mixtures thereof;

ii) said active ingredient is a cosmetic component selected from the group consisting of astringents, emollients, vitamins, moisturizers, abrasives, anti-acne agents, surfactants, aloe, and mixtures thereof;

iii) said active ingredient is a laundry adjunct selected from the group consisting of enzymes, bleaching systems, fabric softener actives, soil release agents, builders, optical brighteners, aesthetic agents, and mixtures thereof;

iv) said active ingredient is a fabric modifying agent selected from the group consisting of dyes, cellulosic crosslinking agents, surface modifying agents, antistatic agents, and mixtures thereof;

v) said active ingredient is a pharmaceutically active agent.

Step (a) of the present process can be conducted in any suitable apparatus. In order to combine ingredients, heating or cooling may be required and the formulator can adjust the temperature as needed. In some cases, the type of mixer or the length of time required to form a homogeneous admixture may vary. In the case wherein a co-solvent or solvent, for example, water, is used, the admixture may be heated to remove the water until the proper viscosity level is achieved.

Step (b) of the present invention relates to forming a foam matrix from the homogeneous admixture. A gas is introduced into the admixture to form a foam. The gas may be introduced directly wherein a gas is metered into the admixture under temperature and pressure conditions suitable to form a foam having the herein described properties, or a compound which liberates a gas upon contact with the homogeneous admixture, upon heating, or upon catalysis can be added.

Non-limiting examples of a gas includes anhydrous air, carbon dioxide, nitrogen, and the like. Once the gas has been introduced and the foam has been formed, the resulting foam will have a relative density of from 0.01 g/cm³ to about 0.95 g/cm³. In one embodiment the foam has a relative density of from 0.05 g/cm³ to about 0.9 g/cm³, whereas in another embodiment the relative density of from 0.1 g/cm³ to about 0.8 g/cm³. A particular embodiment of the present invention relates to an article comprising a foam having a relative density of from 0.1 g/cm³ to about 0.5 g/cm³.

For the purposes of the present invention the term "relative density" is defined herein as "the ratio of the density of the foam component of the sum of the partial densities of all the bulk materials which form the foam component, which can be expressed by the formula:

$$\rho^*_{foam} = \frac{\rho_{foam}}{\rho_{bulk}} = \frac{\rho_{foam}}{\sum_{i=1}^{i=n} \chi_i \rho_i}$$

wherein $\chi_i$ is the volume fraction of the material component i and $\rho_i$ is the density.

In addition, the foam matrix will have an elastic modulus of less than 1 GPa (giga Pascal, giga Newton/m²). Another aspect of the present invention relates to embodiments wherein 10 GPa. For the purposes of the present invention the elastic modulus is measured using a Perkin-Elmer DMA 7e. The flexibility and yield strength of the foam matrix is an element which is key to effective delivery of the active ingredient by the article of manufacture produced by the process of the present invention. In one embodiment, as measured by the DMA 7e instrument, the foam has a relative yield strain greater than about 2%, while another embodiment requires a yield strain greater than 15%. One aspect of the present invention relates to a foam having a yield strain greater than about 50%.

The formulator and artisan of ordinary skill will recognize that the properties of the foam matrix are inextricably linked in various ways, for example, the elastic modulus is related to the relative density by the relationship defined by the formula:

$$\frac{E^*}{E_S} \approx \left(\frac{\rho^*}{\rho_S}\right)^2$$

wherein $E^*$ is the elastic modulus of the foam component, and $E_s$ is the elastic modulus for the polymeric material. Therefore, semi-rigid or stiff polymeric materials having a relatively high $E_s$ can be converted into pliable, flexible foams during step (b) wherein a gas is introduced into the homogeneous admixture, or by the use of a solvent or plasticizer in step (a).

In addition to the relative density requirement for the foam produced in step (b), the foam matrix has an elastic modulus of less than 10 GPa. Another aspect of the present invention relates to foams having an elastic modulus of less than 1 GPa.

Step (c) is an optional shaping or forming step wherein the foam matrix formed in step (b) is cut, sized, ground, or otherwise formed into a shape. This step can be performed by the formulator as a final step, or the bulk material may be fashioned by another formulator within a different process matrix.

In one embodiment, the foam produced in step (b) is formed into a granule having an average size of from 10 to 2000 microns. In another embodiment said granule has an average size of from 50 to 2000 microns, or alternatively an average size of from 100 to 1500 microns. Another embodiment of this aspect has an average size of from 200 to 1000 microns.

However, the formulator is not limited to granules but said foam matrix can be formed into a sheet said sheet having a mean thickness of from about 0.01 microns to about 100,000 microns, whereas another embodiment has a mean thickness of from about 0.05 microns to about 50,000 microns. Another embodiment of the sheet aspect has a mean thickness of from about 0.1 microns to about 30,000 microns.

One aspect of the present invention relates to coating the foam matrix with one or more materials which can provide a property to the surface of the foam. Desirable properties include the use of a material which provides a water barrier to atmospheric moisture but which upon immersion, or immersion and agitation provide for a water soluble delivery. Articles of manufacture, or forms of the foam matrix may be intended by the formulator to be broken up into fragments by the formulator and the coating may be only slightly water soluble. In the case wherein the foam matrix may be friable, as well as elastic the formulator can use any optional coating.

One embodiment of the coating is to apply a solid phase of polyvinyl alcohol which may solublize at higher use temperatures and thereby further regulate the release rate of the active ingredient. The formulator is not restricted to any aspect of a coating provided the water-soluble foam matrix is capable of delivering the active ingredients.

Active Ingredients

The following are non-limiting active ingredients which can be delivered by the water-soluble foam matrix of the present invention.

Surfactants

Nonlimiting examples of surfactants which can be delivered by the articles of manufacture of the present invention or which can be combined in step (a) of the present invention include those readily known by the laundry or cleaning formulator and which include:

a) $C_{11}$–$C_{18}$ alkyl benzene sulfonates (LAS);
b) $C_6$–$C_{18}$ mid-chain branched aryl sulfonates (BLAS);
c) $C_{10}$–$C_{20}$ primary, α or ω-branched, and random alkyl sulfates (AS);
d) $C_{14}$–$C_{20}$ mid-chain branched alkyl sulfates (BAS);
e) $C_{10}$–$C_{18}$ secondary (2,3) alkyl sulfates as described in U.S. Pat. No. 3,234,258 Morris, issued Feb. 8, 1966; U.S. Pat. No. 5,075,041 Lutz, issued Dec. 24, 1991; U.S. Pat. No. 5,349,101 Lutz et al., issued Sep. 20, 1994; and U.S. Pat. No. 5,389,277 Prieto, issued Feb. 14, 1995 each incorporated herein by reference;
f) $C_{10}$–$C_{18}$ alkyl alkoxy sulfates ($AE_xS$) wherein preferably x is from 1–7;
g) $C_{14}$–$C_{20}$ mid-chain branched alkyl alkoxy sulfates ($BAE_xS$);
h) $C_{10}$–$C_{18}$ alkyl alkoxy carboxylates preferably comprising 1–5 ethoxy units;
i) $C_{12}$–$C_{18}$ alkyl ethoxylates, $C_6$–$C_{12}$ alkyl phenol alkoxylates wherein the alkoxylate units are a mixture of ethyleneoxy and propyleneoxy units, $C_{12}$–$C_{18}$ alcohol and $C_6$–$C_{12}$ alkyl phenol condensates with ethylene oxide/propylene oxide block polymers inter alia Pluronic® ex BASF which are disclosed in U.S. Pat. No. 3,929,678 Laughlin et al., issued Dec. 30, 1975, incorporated herein by reference;
j) $C_{14}$–$C_{22}$ mid-chain branched alkyl alkoxylates, $BAE_x$;
k) Alkylpolysaccharides as disclosed in U.S. Pat. No. 4,565,647 Llenado, issued Jan. 26, 1986, incorporated herein by reference;
l) Pseudoquat surfactants having the formula:

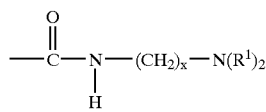

wherein R is $C_4$–$C_{10}$ alkyl, $R^1$ is selected from the group consisting of $C_1$–$C_4$ alkyl, —$(CH_2CHR^2O)_yH$, and mixtures thereof; $R^2$ is hydrogen, ethyl, methyl, and mixtures thereof; y is from 1 to 5; x is from 2 to 4; for the purposes of the present invention, a particularly useful pseudoquat surfactant comprises R equal to an admixture of $C_8$–$C_{10}$ alkyl, $R^1$ is equal to methyl; and x equal to 3; these surfactants are described in U.S. Pat. No. 5,916,862 Morelli et al., issued Jun. 29, 1999 included herein by reference;
m) Polyhydroxy fatty acid amides having the formula:

wherein $R^7$ is $C_5$–$C_{31}$ alkyl; $R^8$ is selected from the group consisting of hydrogen, $C_1$–$C_4$ alkyl, $C_1$–$C_4$ hydroxyalkyl, Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. These surfactants are described in U.S. Pat. No. 5,489,393 Connor et al., issued Feb. 6, 1996; and U.S. Pat. No. 5,45,982 Murch et al., issued Oct. 3, 1995, both incorporated herein by reference.

The amount of surfactant which is added in step (a) will be predicated upon the needs of the formulator and upon the viscosity requirements of step (a) as well as the mechanical properties of the final foam.

Bleaching System

On embodiment of the present invention relates to delivery of a foam matrix stabilized bleaching system. The following is a non-limiting example of a bleaching system which can be delivered by a water-soluble foam matrix as described herein.

i) from about 40%, in one embodiment from about 50% to about 100%, in other embodiments: from about 60% to about 95%, or to about 80% by weight, of the bleaching system, a source of hydrogen peroxide;
ii) optionally from about 0.1%, in other embodiments from about 0.5% to about 60%; while another embodiment relates to about 40% by weight, of the beaching system, a beach activator;
iii) optionally from about 1 ppb (0.0000001%), in yet other embodiments from about 100 ppb (0.00001%); from about 500 ppb (0.00005%); from about 1 ppm (0.0001%) up to, in one embodiment, about 99.9% by weight of the composition, of a transition-metal bleach catalyst;
iv) optionally from about 0.1% by weight, of a pre-formed peroxygen bleaching agent.

Laundry and Cleaning Adjunct Active Ingredients

The following are non-limiting examples of adjunct laundry ingredients (non-surfactant ingredients) which are active ingredients which can be delivered alone or in combination with a detersive surfactant. These ingredients include builders, optical brighteners, soil release polymers, dye transfer agents, dispersents, enzymes, suds suppressers, dyes, perfumes, colorants, filler salts, hydrotropes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

Builders—The foam matrices of the present invention can comprise a builder. The following are examples of builders.

Examples of carbonate builders are the alkaline earth and alkali metal carbonates as disclosed in German Patent Application No. 2,321,001 published on Nov. 15, 1973.

Aluminosilicate builders include those having the empirical formula:

wherein z and y are integers of at least 6, the molar ratio of z to y is in the range from 1.0 to about 0.5, and x is an integer from about 15 to about 264, known as Zeolite A, Zeolite P (B), Zeolite MAP and Zeolite X. In one embodiment, the crystalline aluminosilicate ion exchange material has the formula:

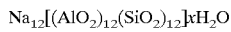

wherein x is from about 20 to about 30, especially about 27. This material is known as Zeolite A. Preferably, the aluminosilicate has a particle size of about 0.1–10 microns in diameter.

Included among the polycarboxylate builders are those disclosed in U.S. Pat. No. 3,128,287 Berg, issued Apr. 7, 1964, and U.S. Pat. No. 3,635,830 Lamberti et al., issued Jan. 18, 1972; U.S. Pat. No. 4,663,071 Bush et al., issued May 5, 1987; U.S. Pat. No. 3,923,679 Rapko, issued Dec. 2, 1975; U.S. Pat. No. 4,158,635 Crutchfield et al., issued Jun. 19, 1979; U.S. Pat. No. 4,120,874 Crutchfield et al., issued Oct. 17, 1978; and U.S. Pat. No. 4,102,903 Crutchfield et al., issued Jul. 25, 1978; all of which are incorporated herein by reference.

Other suitable builders are disclosed in U.S. Pat. No. 4,566,984, Bush, issued Jan. 28, 1986; U.S. Pat. No. 4,144,226, Crutchfield et al., issued Mar. 13, 1979 and in U.S. Pat. No. 3,308,067, Diehl, issued Mar. 7, 1967 and U.S. Pat. No. 3,723,322; incorporated herein by reference. Phosphonate builders such as ethane-1-hydroxy-1,1-diphosphonate and other known phosphonates as described in U.S. Pat. Nos. 3,159,581; 3,213,030; 3,422,021; 3,400,148 and 3,422,137 included herein by reference.

Dispersants

The matices of the present invention may comprise one or more polyalkyleneimine dispersants as described in U.S. Pat. No. 4,597,898 Vander Meer, issued Jul. 1, 1986; European Patent Application 111,965 Oh and Gosselink, published Jun. 27, 1984; European Patent Application 111,984 Gosselink, published Jun. 27, 1984; European Patent Application 112,592 Gosselink, published Jul. 4, 1984; U.S. Pat. No. 4,548,744 Connor, issued Oct. 22, 1985; and U.S. Pat. No. 5,565,145 Watson et al., issued Oct. 15, 1996; all of which are included herein by reference. However, any suitable clay/soil dispersant or anti-redepostion agent can be used in the laundry compositions of the present invention.

Soil Release Agents

The matrices according to the present invention may comprise one or more soil release agents described in U.S. Pat. No. 5,843,878 Gosselink et al., issued Dec. 1, 1998; U.S. Pat. No. 5,834,412 Rohrbaugh et al., issued Nov. 10, 1998; U.S. Pat. No. 5,728,671 Rohrbaugh et al., issued Mar. 17, 1998; U.S. Pat. No. 5,691,298 Gosselink et al., issued Nov. 25, 1997; U.S. Pat. No. 5,599,782 Pan et al., issued Feb. 4, 1997; U.S. Pat. No. 5,415,807 Gosselink et al., issued May 16, 1995; U.S. Pat. No. 5,182,043 Morrall et al., issued Jan. 26, 1993; U.S. Pat. No. 4,956,447 Gosselink et al., issued Sep. 11, 1990; U.S. Pat. No. 4,976,879 Maldonado et al. issued Dec. 11, 1990; U.S. Pat. No. 4,968,451 Scheibel et al., issued Nov. 6, 1990; U.S. Pat. No. 4,925,577 Borcher, Sr. et al., issued May 15, 1990; U.S. Pat. No. 4,861,512 Gosselink, issued Aug. 29, 1989; U.S. Pat. No. 4,877,896 Maldonado et al., issued Oct. 31, 1989; U.S. Pat. No. 4,771,730 Gosselink et al., issued Oct. 27, 1987; U.S. Pat. No. 711,730 Gosselink et al., issued Dec. 8, 1987; U.S. Pat. No. 4,721,580 Gosselink issued Jan. 26, 1988; U.S. Pat. No. 4,000,093 Nicol et al., issued Dec. 28, 1976; U.S. Pat. No. 3,959,230 Hayes, issued May 25, 1976; U.S. Pat. No. 3,893,929 Basadur, issued Jul. 8, 1975; and European Patent Application 0 219 048, published Apr. 22, 1987 by Kud et al.

Further suitable soil release agents are described in U.S. Pat. No. 4,201,824 Voilland et al.; U.S. Pat. No. 4,240,918 Lagasse et al.; U.S. Pat. No. 4,525,524 Tung et al.; U.S. Pat. No. 4,579,681 Ruppert et al.; U.S. Pat. No. 4,220,918; U.S. Pat. No. 4,787,989; EP 279,134 A, 1988 to Rhone-Poulenc Chemie; EP 457,205 A to BASF (1991); and DE 2,335,044 to Unilever N.V., 1974; all incorporated herein by reference.

Enzymes

The matrices of the present invention may comprise one or more enzymes. Preferred enzymes include the commercially available lipases, cutinases, amylases, neutral and alkaline proteases, cellulases, endolases, esterases, pectinases, lactases and peroxidases conventionally incorporated into detergent compositions. Suitable enzymes are discussed in U.S. Pat. Nos. 3,519,570 and 3,533,139. Preferred commercially available protease enzymes include those sold under the tradenames Alcalase, Savinase, Primase, Durazym, and Esperase by Novo Industries A/S (Denmark), those sold under the tradename Maxatase, Maxacal and Maxapem by Gist-Brocades, those sold by Genencor International, and those sold under the tradename Opticlean and Optimase by Solvay Enzymes. Preferred amylases include, for example, α-amylases obtained from a special strain of B licheniformis, described in more detail in GB-1, 269,839 (Novo). Preferred commercially available amylases include for example, those sold under the tradename Rapidase by Gist-Brocades, and those sold under the tradename Termamyl, Duramyl and BAN by Novo Industries A/S. Highly preferred amylase enzymes maybe those described in PCT/US 9703635, and in WO95/26397 and WO96/23873. The lipase may be fungal or bacterial in origin being obtained, for example, from a lipase producing strain of *Humicola* sp., *Thermomyces* sp. or *Pseudomonas* sp. including *Pseudomonas pseudoalcaligenes* or *Pseudomas fluorescens*. Lipase from chemically or genetically modified mutants of these strains are also useful herein. A preferred lipase is derived from Pseudomonas pseudoalcaligenes, which is described in Granted European Patent, EP-B-0218272. Another preferred lipase herein is obtained by cloning the gene from *Humicola lanuginosa* and expressing the gene in *Aspergillus oryza*, as host, as described in European Patent Application, EP-A-0258 068, which is commercially available from Novo Industri A/S, Bagsvaerd, Denmark, under the trade name Lipolase. This lipase is also described in U.S. Pat. No. 4,810,414, Huge-Jensen et al, issued Mar. 7, 1989.

The matrices of the present invention can also relate to the delivery of a personal care adjunct ingredient, for example, ingredients which can reduce dermatitis or compounds which can help the healing of the skin, metal-containing compounds, in particular zinc-containing compounds, vitamins and cortisone's, and also compounds to soften the skin such as vaseline, lanolin, and other actives typically employed by pharmaceutical and cosmetic manufactures.

EXAMPLE 1

An APV lab extruder (model MP19CH) was used to make the following water-soluble foam component.

A viscous mixture of 1600 gr water, 613 gr glycerine (Sigma/Aldrich 13487-2) and 1000 gr Lineair alkyl benzene sulphonate sodium salt (LAS) surfactant paste (76% active) was made using an overhead stirrer.

Powdered polyvinyl alcohol (Sigma/Aldrich P8136) (1900 gr) was added to the extruder via the powder feed, and the viscous mixture was added slightly downstream of the powder via an injection system on a side entry port. Air was added with the liquid (by aerating with a Kenwood-type food mixer), at a volume ratio of 3 parts air to 1 part viscous mixture.

The viscous mixture feed was run at a constant rate of about 100 gr/min, and the powder PVA feed about 60 gr/min. Screw speed of the extruder was 400 RPM. The last 4 sections of the extruder barrel were heated to 65° C. Pressure just before the extruder exit was approximately 25 bar. The approximate viscosity of the viscous mixture comprising the PVA powder (in the extruder; without air incorporation) was 200 Pa.s at 1.7 s$^{-1}$ The foam component produced at the extruder outlet was collected this was further shaped by and adding it in petri-dish moulds to give a series of foam discs, which were allowed to dry in ambient conditions. This drying was complete in <2 hours, giving a dry foam that was water-soluble, air-stable, elastic, and could be easily handled. The dry foam had a density of approx. 0.24 g/cm3 and a remaining water content of approx. 5% by weight.

The above process is repeated with (replacing the 1000 gr LAS paste):
1000 gr enzyme (protease, lipase, amylase, cellulase or mixtures thereof);
1000 gr of a mixture of (weight %) 30% LAS, 20% perfume oil, 20% soap, 10% bleach, 20% cationic surfactant;
1000 gr of a mixture of (weight %) 80% betaine surfactant, amphoteric surfactant, cationic surfactant, anionic surfactant and/or nonionic surfactant (70% active paste of one or more of these surfactants) and 20% perfume oil;
1000 gr of a 70% active paste of cationic fabric softening agent or cationic hair conditioner;
1000 gr of a mixture of (by weight) 40% sodium percarbonate 30% activator, 30% surfactant.

What is claimed is:

1. A process for preparing a water soluble, active ingredient loaded foam matrix said process comprising the steps of:
   a.) admixing a water-soluble polymer and an active ingredient to form a homogeneous admixture, said admixture having a viscosity of at least 150 Pa-sec;
   b.) introducing a gas or a compound capable of releasing a gas into said admixture to form a water soluble foam matrix having a relative density of from 0.01 g/cm$^3$ to about 0.95 g/cm$^3$ and an elastic modulus of less than 10 GPa; and
   c.) optionally, shaping said matrix.

2. A process according to claim 1 wherein said homogenous admixture has a viscosity of at least 200 Pa-sec.

3. A process according to claim 2 wherein said homogenous admixture has a viscosity of at least 250 Pa-sec.

4. A process according to claim 3 wherein said homogenous admixture has a viscosity of at least 300 Pa-sec.

5. A process according to claim 4 wherein said homogenous admixture has a viscosity of at least 350 Pa-sec.

6. A process according to claim 1 wherein said water-soluble polymer is selected from the group consisting of polyvinyl alcohol, polyvinyl pyrrolidone, polyalkylene oxides, cellulose ethers, polycarboxylic acids, polyamino acids, polyacrylamide and mixtures thereof.

7. A process according to claim 6 wherein said polymer is polyvinyl alcohol, hydroxypropyl methylcellulose, maleic/acrylic acid copolymers, and mixtures thereof.

8. A process according to claim 1 wherein said active ingredient is a detersive surfactant selected from the group consisting of anionic, cationic, nonionic, zwitterionic, ampholytic surfactants and mixtures thereof.

9. A process according to claim 1 wherein said active ingredient is a cosmetic component selected from the group consisting of astringents, emollients, vitamins, moisturizers, abrasives, anti-acne agents, surfactants, aloe, and mixtures thereof.

10. A process according to claim 1 wherein said active ingredient is a laundry adjunct selected from the group consisting of enzymes, bleaching systems, fabric softener actives, soil release agents, builders, optical brighteners, aesthetic agents, and mixtures thereof.

11. A process according to claim 1 wherein said active ingredient is a fabric modifying agent selected from the group consisting of dyes, cellulosic crosslinking agents, surface modifying agents, anti-static agents, and mixtures thereof.

12. A process according to claim 1 wherein said active ingredient is a pharmaceutically active agent.

13. A process according to claim 1 wherein step (a) further comprises admixing one or more dissolution aids.

14. A process according to claim 1 wherein step (a) further comprises admixing one or more pH adjusting agents.

15. A process according to claim 1 wherein step (a) further comprises admixing one or more stabilizing agents.

16. A process according to claim 1 wherein said foam matrix has a relative density of from 0.05 g/cm$^3$ to about 0.9 g/cm$^3$.

17. A process according to claim 16 wherein said foam matrix has a relative density of from 0.1 g/cm$^3$ to about 0.5 g/cm$^3$.

18. A process according to claim 1 wherein said foam matrix has an elastic modulus of less than 1 GPa.

19. A process according to claim 1 wherein said gas is selected from the group consisting of nitrogen, carbon dioxide, anhydrous air, and mixtures thereof.

20. A process according to claim 1 wherein said foam matrix is shaped by extruding said foam matrix formed in step (b).

21. A process according to claim 1 wherein said foam matrix is formed into a granule.

22. A process according to claim 21 wherein said granule has an average size of from 10 to 2000 microns.

23. A process according to claim 22 wherein said granule has an average size of from 50 to 2000 microns.

24. A process according to claim 23 wherein said granule has an average size of from 100 to 1500 microns.

25. A process according to claim 24 wherein said granule has an average size of from 200 to 1000 microns.

26. A process according to claim 1 wherein said foam matrix is formed into a sheet said sheet having a mean thickness of from about 0.01 microns to about 100,000 microns.

27. A process according to claim 26 wherein said foam matrix is formed into a sheet said sheet having a mean thickness of from about 0.05 microns to about 50,000 microns.

28. A process according to claim wherein said foam matrix is formed into a sheet said sheet having a mean thickness of from about 0.1 microns to about 30,000 microns.

29. An article of manufacture comprising:
   (i) a water-soluble, polymeric foam matrix having a relative density of from 0.01 g/cm$^3$ to about 0.95 g/cm$^3$ and an elastic modulus of less than 10 GPa;

(ii) an active ingredient dispersed throughout said matrix; and (iii) optionally, a coating.

30. An article according to claim 29 wherein said water-soluble polymeric foam matrix comprises a polymer selected from the group consisting of polyvinyl alcohol, polyvinyl pyrrolidone, polyalkylene oxides, cellulose ethers, polycarboxylic acids, polyamino acids, polyacrylamide, and mixtures thereof.

31. An article according to claim 29 wherein said active ingredient is a detersive surfactant selected from the group consisting of anionic, cationic, nonionic, zwitterionic, ampholytic surfactants and mixtures thereof.

32. An article according to claim 29 wherein said active ingredient is a cosmetic component selected from the group consisting of astringents, emollients, vitamins, moisturizers, abrasives, anti-acne agents, surfactants, aloe, and mixtures thereof.

33. An article according to claim 29 wherein said active ingredient is a laundry adjunct selected from the group consisting of enzymes, bleaching systems, fabric softener actives, soil release agents, builders, optical brighteners, aesthetic agents, and mixtures thereof.

34. An article according to claim 29 said active ingredient is a fabric modifying agent selected from the group consisting of dyes, cellulosic crosslinking agents, surface modifying agents, anti-static agents, and mixtures thereof.

35. An article according to claim 29 wherein said active ingredient is a pharmaceutically active agent.

36. An article according to claim 29 wherein said water-soluble, polymeric foam matrix has a relative density of from 0.1 $g/cm^3$ to about 0.5 $g/cm^3$.

37. An article according to claim 29 wherein said water-soluble, polymeric foam matrix has an elastic modulus of less than 1 GPa.

38. An article according to claim 29 wherein said article is a granule material having an average size of from 200 to 1000 microns.

39. An article according to claim 29 wherein said article is a sheet having a mean thickness of from about 0.1 microns to about 30,000 microns.

* * * * *